United States Patent [19]
Horstman et al.

[11] Patent Number: 5,851,079
[45] Date of Patent: Dec. 22, 1998

[54] SIMPLIFIED UNDIRECTIONAL TWIST-UP DISPENSING DEVICE WITH INCREMENTAL DOSING

[75] Inventors: Richard L. Horstman, Cincinnati, Ohio; Reuben E. Oder, Union, Ky.; Robert L. Prosise, Cincinnati, Ohio; Kathleen A. Pieper, White Hall, Md.; Genevieve R. Smith, Fairfield; Robert S. Dirksing, Cincinnati, both of Ohio; Susan B. Baggott, Owings Mills, Md.

[73] Assignee: The Procter & Gamble Company, Cincinnati, Ohio

[21] Appl. No.: 738,129

[22] Filed: Oct. 25, 1996

[51] Int. Cl.⁶ .......................... A46B 11/02; A45D 40/06
[52] U.S. Cl. .................... 401/174; 401/172; 401/194; 401/266; 401/288
[58] Field of Search .................... 401/174, 194, 401/288, 266, 172

[56] References Cited

U.S. PATENT DOCUMENTS

| | | | |
|---|---|---|---|
| Re. 30,659 | 6/1981 | Otake et al. | 401/209 |
| D. 175,548 | 9/1955 | Kane | D9/2 |
| D. 299,973 | 2/1989 | Campello et al. | D28/7 |
| D. 306,354 | 2/1990 | Konose | D28/7 |
| D. 306,355 | 2/1990 | Shinohara | D28/7 |
| D. 306,914 | 3/1990 | Shinohara | D28/7 |
| D. 318,538 | 7/1991 | Shinohara | D28/7 |
| D. 325,264 | 4/1992 | Shinohara | D27/7 |
| D. 330,442 | 10/1992 | Fukazawa | D28/7 |
| D. 353,397 | 12/1994 | Banik | D19/66 |
| 835,606 | 11/1906 | Frimand . | |
| 1,599,660 | 9/1926 | Little et al. . | |
| 1,644,173 | 10/1927 | Carr . | |
| 1,919,859 | 7/1933 | Phillips . | |
| 1,950,324 | 3/1934 | Powers | 206/56 |
| 1,994,890 | 3/1935 | Kallenbach | 15/133 |
| 2,068,213 | 1/1937 | Wilson | 15/134 |
| 2,094,700 | 10/1937 | Gunn | 221/60 |

(List continued on next page.)

FOREIGN PATENT DOCUMENTS

| | | | |
|---|---|---|---|
| 0258799 | 8/1987 | European Pat. Off. | B65D 83/00 |
| 0434326A1 | 12/1990 | European Pat. Off. | B65D 83/00 |
| 2623-426-A | 5/1989 | France . | |
| 2 198 037 | 6/1988 | United Kingdom . | |
| 2229791 | 10/1990 | United Kingdom | 401/174 |
| 2 208 471 | 3/1991 | United Kingdom . | |
| 2 211 081 | 7/1991 | United Kingdom . | |
| WO 91/015135 A1 | 3/1991 | WIPO | A45D 34/04 |
| 9115135 | 10/1991 | WIPO | 401/174 |

*Primary Examiner*—Steven A. Bratlie
*Attorney, Agent, or Firm*—Rodney M. Young

[57] ABSTRACT

A unidirectional twist-up dispensing device with incremental dosing for dispensing a product is provided. This twist-up dispensing device includes a hollow housing defining a chamber having an open dispensing end and an open actuating end having a interior surface. A piston located within the chamber being limited to translational movement within the chamber. The piston having a top side facing the dispensing end of the housing forming a variable volume portion of the chamber for storing the product. The piston also having a threaded rod extending therefrom opposite the top side. An actuator having a threaded aperture therethrough that engages the interior surface at the actuating end of the housing is also provided. The threaded aperture is concentric in the actuator and the actuator is adapted to rotate with respect to the housing in only one direction. The threaded rod engages the threaded aperture such that advancement of the piston toward the dispensing end occurs when the actuator is rotated, thereby causing the product to be dispensed. An applicator can be attached to the dispensing end of the housing in fluid communication with the variable volume portion of the chamber wherein the product is dispensed through the applicator. The applicator comprises a ferrule and an application portion. The ferrule is attached to the dispensing end of the housing and the application portion has at least one orifice located therein. Several versions of the applicator are illustrated, including a fiber brush and a flocked application surface.

17 Claims, 6 Drawing Sheets

U.S. PATENT DOCUMENTS

| | | | |
|---|---|---|---|
| 2,196,379 | 4/1940 | Bender | 221/79 |
| 2,309,861 | 2/1943 | Mureau | 15/137 |
| 2,314,539 | 3/1943 | Hollenbeck | 15/139 |
| 2,374,065 | 4/1945 | Worthington | 15/137 |
| 2,442,503 | 6/1948 | Melnikoff | 132/88.7 |
| 2,604,104 | 7/1952 | Kruck | 132/88.7 |
| 2,629,889 | 3/1953 | Lengyel | 15/137 |
| 2,763,881 | 9/1956 | Riel | 15/137 |
| 2,816,309 | 12/1957 | Worth et al. | 15/137 |
| 2,908,925 | 10/1959 | Reitknecht | 15/137 |
| 2,913,748 | 11/1959 | Felter | 15/139 |
| 2,917,765 | 12/1959 | Jakubowski | 15/137 |
| 3,002,517 | 10/1961 | Pitton | 132/85 |
| 3,212,120 | 10/1965 | Gentile | 15/558 |
| 3,226,762 | 1/1966 | Norman | 15/558 |
| 3,369,543 | 2/1968 | Ronco | 128/269 |
| 3,459,482 | 8/1969 | Fears | 401/15 |
| 3,468,612 | 9/1969 | Aston | 401/174 X |
| 3,481,676 | 12/1969 | Schwartzman | 401/134 |
| 3,756,730 | 9/1973 | Spatz | 401/174 |
| 3,771,166 | 11/1973 | Tuilos | 346/140 |
| 3,807,881 | 4/1974 | Seidler | 401/175 |
| 3,825,021 | 7/1974 | Seidler | 132/88.7 |
| 3,850,531 | 11/1974 | Ackermann | 401/65 |
| 3,881,828 | 5/1975 | Jones | 401/199 |
| 3,917,417 | 11/1975 | Lang | 401/72 |
| 3,942,903 | 3/1976 | Dickey et al. | 401/198 |
| 4,119,756 | 10/1978 | Midorikawa | 428/295 |
| 4,139,127 | 2/1979 | Gentile | 222/390 |
| 4,201,491 | 5/1980 | Kohler | 401/264 |
| 4,384,589 | 5/1983 | Morris | 132/88.5 |
| 4,421,809 | 12/1983 | Bish et al. | 428/90 |
| 4,446,965 | 5/1984 | Montiel | 206/205 |
| 4,551,038 | 11/1985 | Baker et al. | 401/265 |
| 4,595,124 | 6/1986 | Duval et al. | 222/39 |
| 4,622,985 | 11/1986 | Jankewitz | 132/88.5 |
| 4,624,594 | 11/1986 | Sasaki et al. | 401/176 |
| 4,708,267 | 11/1987 | Sieverding et al. | 222/211 |
| 4,749,618 | 6/1988 | Kawaguchi et al. | 428/375 |
| 4,762,433 | 8/1988 | Bergeson et al. | 401/206 |
| 4,795,218 | 1/1989 | Seidler | 300/21 |
| 4,844,250 | 7/1989 | Holoubek et al. | 222/107 |
| 4,856,925 | 8/1989 | Konose | 401/290 |
| 4,865,231 | 9/1989 | Wiercinski | 222/390 |
| 4,874,117 | 10/1989 | Kay et al. | 222/487 |
| 4,887,924 | 12/1989 | Green | 401/261 |
| 4,946,302 | 8/1990 | Uchida | 401/288 |
| 4,954,000 | 9/1990 | Gueret | 401/68 |
| 4,961,663 | 10/1990 | Iwamoto et al. | 401/78 |
| 4,966,479 | 10/1990 | Idec et al. | 401/68 |
| 4,978,242 | 12/1990 | Konose | 401/129 |
| 4,987,911 | 1/1991 | Powers | 132/320 |
| 4,997,299 | 3/1991 | Ohba | 401/75 |
| 5,000,356 | 3/1991 | Johnson et al. | 222/391 |
| 5,007,754 | 4/1991 | Zierhut | 401/174 |
| 5,007,755 | 4/1991 | Thompson | 401/175 |
| 5,011,317 | 4/1991 | Gueret | 401/66 |
| 5,019,033 | 5/1991 | Geria | 604/2 |
| 5,026,195 | 6/1991 | Kimura | 401/283 |
| 5,035,525 | 7/1991 | Konose | 401/278 |
| 5,042,955 | 8/1991 | Moscatelli | 401/269 |
| 5,073,057 | 12/1991 | Lathrop et al. | 401/206 |
| 5,085,352 | 2/1992 | Sasaki et al. | 222/327 |
| 5,097,853 | 3/1992 | Nehashi | 132/320 |
| 5,119,838 | 6/1992 | Nakazima | 132/108 |
| 5,123,431 | 6/1992 | Wilson | 132/320 |
| 5,124,205 | 6/1992 | Raynolds et al. | 428/364 |
| 5,131,773 | 7/1992 | Gueret | 401/68 |
| 5,137,388 | 8/1992 | Kimura | 401/278 |
| 5,176,461 | 1/1993 | Kimura | 401/279 |
| 5,234,136 | 8/1993 | Kopis | 222/391 |
| 5,255,990 | 10/1993 | Dornbusch et al. | 401/68 |
| 5,299,877 | 4/1994 | Birden | 401/206 |
| 5,320,442 | 6/1994 | Yanagisawa et al. | 401/172 |
| 5,372,444 | 12/1994 | Lhuisset | 401/175 |
| 5,396,913 | 3/1995 | Wallschlaeger | 132/320 |
| 5,401,112 | 3/1995 | Dornbusch et al. | 401/68 |
| 5,454,660 | 10/1995 | Sakurai et al. | 401/266 |
| 5,478,552 | 12/1995 | Hasegawa | 424/63 |
| 5,480,250 | 1/1996 | Birden | 401/199 |
| 5,556,215 | 9/1996 | Hori | 401/199 |

SIMPLIFIED UNDIRECTIONAL TWIST-UP DISPENSING DEVICE WITH INCREMENTAL DOSING

FIELD OF THE INVENTION

The present invention relates to twist-up type dispensing devices; and more particularly, to unidirectional twist-up type dispensing devices with incremental dosing.

BACKGROUND OF THE INVENTION

Numerous arrangements and configurations of twist-up dispensing packages for dispensing a quantity of fluid from an internal storage reservoir are known in the art. Various types of twist-up dispensing devices are available for dispensing spreadable or flowable products which then apply these products onto a surface. Such dispensers have been employed for dispensing many types of fluids and various other products such as creams, semisolids, gels, liquids, pastes, and the like. Twist-up as used herein refers to a helical advancing or screw advancing type mechanism. Typically, in this type of dispenser, the product is placed within a hollow container body having openings in a dispensing end with the other end being closed. The product is advanced toward the dispensing end by manual rotation of a rotary actuator, which drives a feed screw and, in turn, an elevator. Moving the elevator into the product pressurizes it, causing the product to be expelled or pushed from the storage reservoir through the openings in the dispensing end and onto an application surface.

In typical twist-up dispensing devices, as long as the rotary actuator is being rotated, product will be dispensed from the dispenser at a uniform rate in a generally continuous fashion. One undesirable effect of this type dispenser is that the user may not be able to visually judge the proper amount of product which should be dispensed. Applying too much product results in product waste and messiness. Many heretofore known and commercially implemented twist-up dispensers have attempted to resolve this problem by employing unidirectional/incremental dosing type dispensers using relatively complex mechanisms.

One approach uses a ratchet and a pawl mechanism to dispense metered quantities of semisolid products. For example, in U.S. Pat. No. 4,595,124 issued to Duval et al. on Jun. 17, 1986, a cylindrical container having a rounded closed applicator end utilizes a dial and screw drive ratchet means along with a base and wrench means that restrains a drive screw from rotation while permitting it to move axially in order to cause the piston to expel the semisolid contents in metered increments. One drawback with this approach is that it creates a twist-up mechanism having numerous, separate and complex structural elements. Attempts have also been made to use unidirectional twist-up dispensing devices for the dispensing of liquid products. For example, in British Patent 2198037 issued on May 9, 1990, a liquid applicator having a rotary control sleeve rotatable in only a single direction uses a rigid cam projection that acts as a detent with respect to a cylindrical cam follower that is urged rearwardly under the influence of a resilient force generated by a coil spring. One drawback with this approach is that the addition of an independent spring element, in order to bias the ratchet mechanism together, increases the complexity and cost of the dispensing device making it a less than desirable alternative.

While it is important to minimize manufacturing costs and simplify the production process, it is also important that such a dispensing device be convenient and easy for the consumer to use. One approach for dispensing creams uses a resilient pawl with an axial ratchet mechanism. For example, in U.S. Pat. No. 4,139,127 issued to Gentile on Feb. 13, 1979, the user is only able to turn a rotatory applicator in a direction which moves a pusher, having a threaded passageway, toward the rotatory applicator thereby dispensing material through openings in the rotatory applicator. One problem inherent with this approach is that the user must grasp and turn the rotatory applicator through which the material is dispensed. Thus, the users hands can come into contact with the material becoming soiled and causing a messy dispensing operation. This condition is exacerbated when an excessive amount of material is unintentionally dispensed. Dispenser configurations of the types mentioned are often complex and expensive to manufacture and are also often difficult or inconvenient for the user to operate.

SUMMARY OF THE INVENTION

One of the objects of this invention is to provide a unidirectional twist-up dispensing device that is simple in design and that minimizes the number of separate components. Another object of this invention is to provide a simplified unidirectional twist-up type dispensing device which includes an incremental dosing feature. Most dispensing devices of this type are, unfortunately, made such that only one type of applicator is intended to be used with the dispenser. Therefore, still another object of this invention is to provide a dispensing device which is versatile enough that various types of applicators can be initially installed during assembly with a common base portion. Dispensing devices incorporating the aforementioned objects can greatly reduce production costs, reduce the overall quantity of components, and reduce the complexity of such dispensing devices.

The present invention provides a twist-up dispensing device for dispensing a product. This twist-up dispensing device includes a hollow housing defining a chamber having an open dispensing end, and an actuating end preferably having an interior surface. Preferably, the interior surface is cylindrical. A piston is located within the chamber and the piston is limited to translational movement within the chamber. The piston has a top side facing the dispensing end of the housing. A variable volume portion of the chamber is formed between the chamber and the top side of the piston. The variable volume portion is for storing the product. The piston also has a threaded rod extending therefrom in a direction opposite the top side. An actuator is also provided, having a threaded aperture therethrough, and the actuator engages the interior surface at the actuating end of the housing. The threaded aperture is concentric within the actuator and the actuator is adapted to rotate with respect to the housing in only one direction. Preferably, a hand wheel is provided that includes the actuator being connected to a grip portion that extends from the actuating end of the housing and, more preferably, the hand wheel is a single piece, unitarily formed from a plastic material. The interior surface includes a lip and at least one detent. The actuator includes a groove engaged with the lip such that the actuator is rotatable but cannot move axially relative to the interior surface. The actuator also has a resilient arm extending outwardly and engaging the detent such that the actuator is rotatable in an advancing direction but not in an opposite direction. Preferably, the resilient arm is inclined radially toward the interior surface and, more preferably, the actuator has at least two resilient arms. The threaded rod engages the threaded aperture such that advancement of the piston toward the dispensing end occurs when the actuator is rotated, thereby causing the product to be dispensed.

The twist-up dispensing device can further comprise an applicator attached to the dispensing end of the housing in fluid communication with the variable volume portion of the chamber wherein the product is dispensed through the applicator. The applicator comprises a ferrule and an application portion. The ferrule is attached to the dispensing end of the housing and the application portion has at least one orifice located therein. A cap that is removable is also provided. The cap sealingly encloses the orifice and the application portion of the applicator.

In another aspect of the present invention, the twist-up dispensing device includes an annular platform affixed to fiber bristles, an interior shoulder within the applicator, and a transition piece positioned within the dispensing end of the housing. The transition piece extends through the ferrule into the application portion of the applicator. The annular platform is captured between the transition piece and the interior shoulder of the applicator positioning the fiber bristles such that the fiber bristles extend through the orifice in the application portion. The transition piece has a passageway therethrough placing the orifice and the fiber bristles in fluid communication with the variable volume portion of the chamber. Preferably, the piston sealingly engages the interior surface. The dispensing end of the hollow housing includes an exterior surface having a ridge and the ferrule of the applicator includes an internal surface having a bead. Preferably, the exterior surface and the internal surface are cylindrical. The bead mates with the ridge forming a snap-fit engagement between the ferrule and the dispensing end thereby attaching the applicator to the housing. In this most preferred embodiment, the product can comprise a fluid and even more preferably, the fluid comprises a cosmetic.

In an alternative embodiment, the application portion further comprises a fiber brush. In another alternative embodiment, the application portion can comprise a flocked application surface.

BRIEF DESCRIPTION OF THE DRAWINGS

While the specification concludes with claims particularly pointing out and distinctively claiming the present invention, it is believed that the present invention will be better understood from the following detailed description in conjunction with the accompanying drawings in which like reference numerals identify identical elements and wherein:

DETAILED DESCRIPTION OF THE INVENTION

Figure 1:
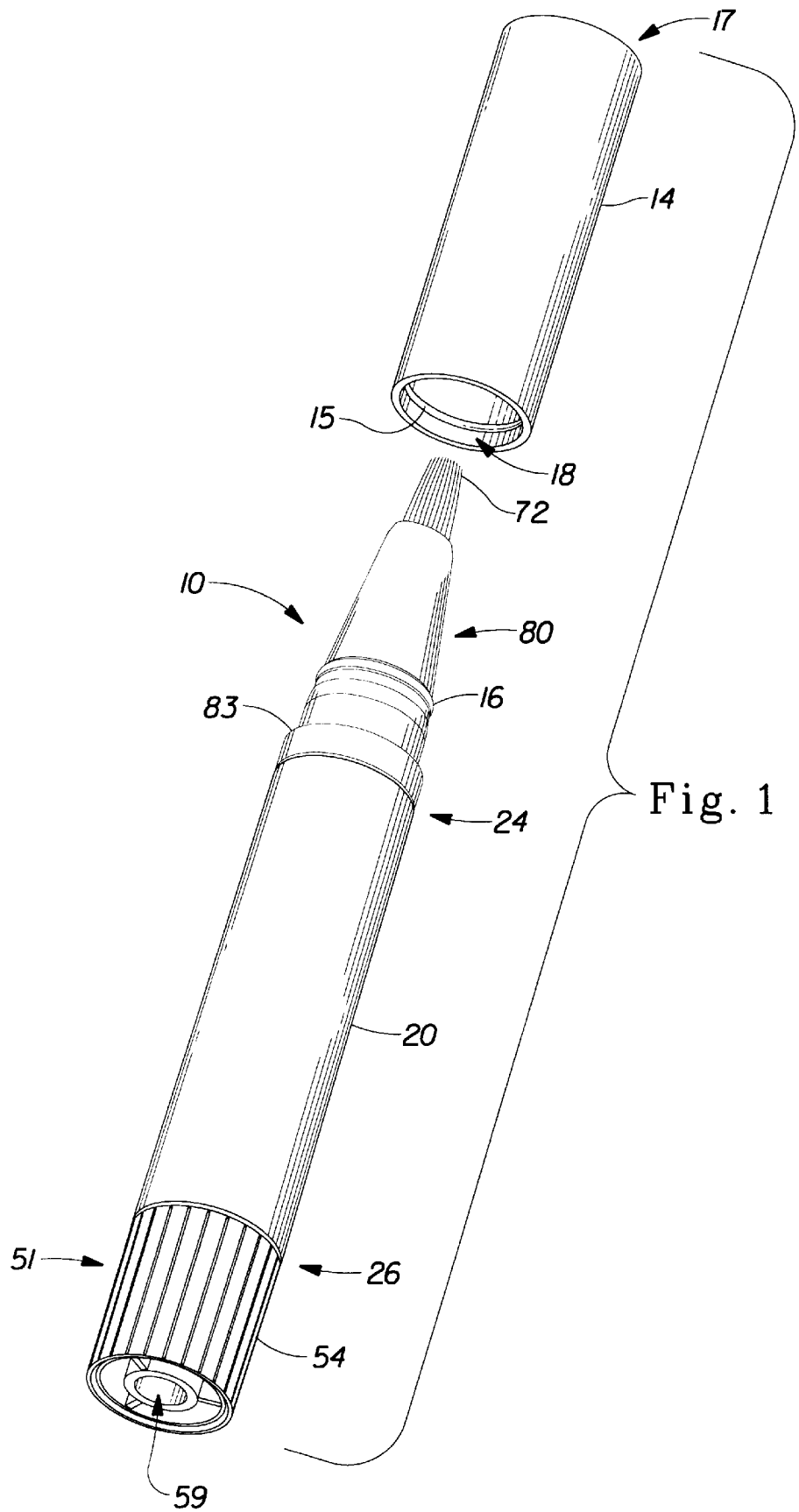
FIG. 1 is a perspective view of a preferred embodiment of the dispensing device of the present invention.

In a particularly preferred embodiment seen in FIG. 1, the present invention provides a twist-up dispensing device, indicated generally as 10, for dispensing a product, such as a fluid, cream, semisolid, gel, paste, liquid, or the like. Dispensing device 10 comprises, in part, a rotatable hand wheel, generally indicated as 51, rotatably connected to a housing 20 which is attached to an applicator, generally indicated as 80. A cap 14 having a closed end 17 and an open end 18 is also provided. Cap 14 is removably connected to dispensing device 10 by frictional engagement with applicator 80.

Figure 2:
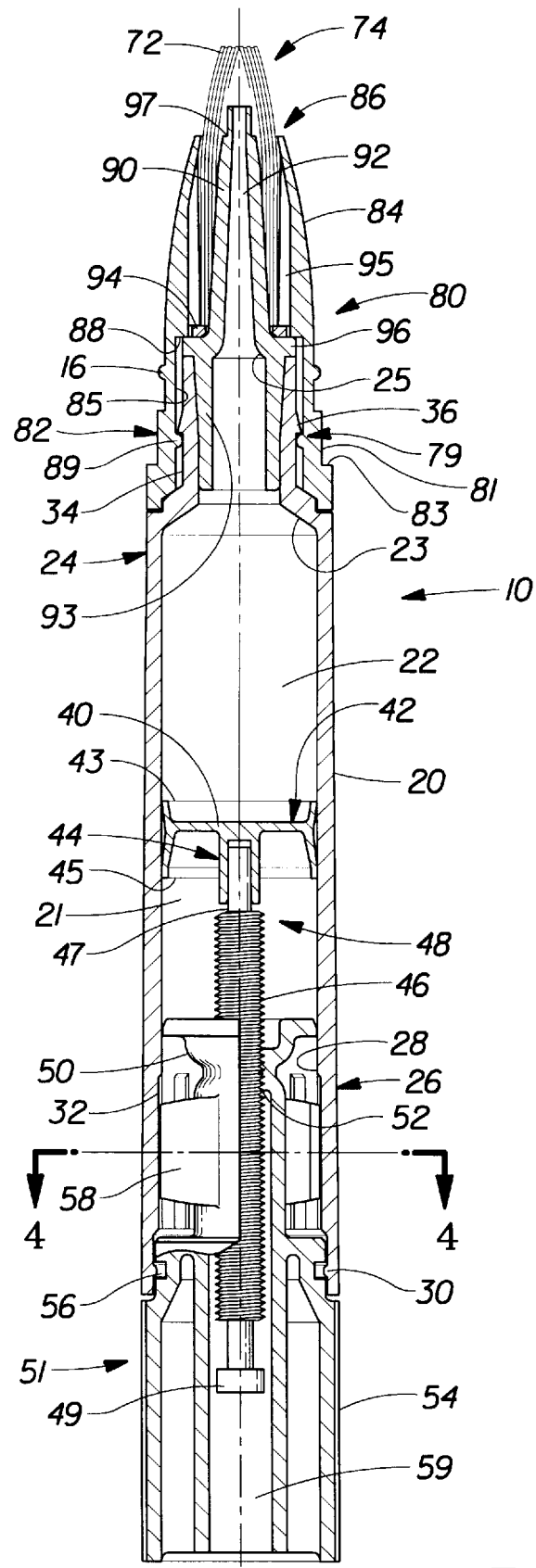
FIG. 2 is a vertical, cross-sectional view of the dispensing device seen in FIG. 1 without the cap.

Referring now to FIG. 2 in which a vertical cross-sectional view of dispensing device 10 is seen, housing 20 is hollow and elongated and has an axis extending lengthwise therethrough. Housing 20 has a chamber 21 therein and includes an open dispensing end 24 located opposite an actuating end 26 with actuating end 26 having an interior surface 28. Preferably interior surface 28 is cylindrical. Cylindrical, as used herein refers to a three-dimensional shape that is elongated while also having a generally circular cross-section. Preferably, interior surface 28 extends from actuating end 26 to dispensing end 24 of housing 20. The cross-sectional shape of chamber 21 can alternatively be of various shapes, such as oval, rectangular, oblong, irregular, or the like. At actuating end 26, interior surface 28 includes a lip 30 and at least one detent 32. Detent 32 comprises a substantially localized indentation, recessed area, or protrusion in interior surface 28. Interior surface 28 can include a plurality of detents 32 and preferably these detents 32 are radially spaced along interior surface 28. Preferably lip 30 is positioned adjacent to and aft of the radially spaced detents 32. Dispensing end 24 can include a first reducer 23 which acts to reduce or decrease the cross section through which product passes when being dispensed. Preferably, first reducer 23 is frusta-conical in shape. Additionally, dispensing end 24 of housing 20 preferably has an exterior surface 34 which includes a ridge 36. Exterior surface 34 is preferably cylindrical. Housing 20 is preferably constructed from a material such as nylon, acrylonitrile butadiene styrene (ABS), polypropylene (PP), polyethylene (PE), styrene-acrylonitrile (SAN), or more preferably, a material such as polybutylene terapthalate (PBT) with ABS, or most preferably, a rubber modified acrylonitrile copolymer which is commercially available as BAREX™ 210 from BP Chemicals can be used.

A piston 40 is located within chamber 21 of housing 20. This piston 40 is preferably limited to axial or translational movement within chamber 21 and preferably does not rotate relative to interior surface 28. Piston 40 has a top-side 42 facing dispensing end 24 of housing 20 and a bottom-side 44 opposite top-side 42. As piston 40 axially translates within chamber 21, top-side 42 of piston 40 forms a variable volume portion 22 within chamber 21. This variable volume portion 22 is used for storing the product that is to be dispensed from the twist-up dispensing device 10. In a preferred embodiment, top-side 42 of piston 40 is provided with an upper-sealing rim 43 which sealingly engages interior surface 28. Bottom-side 44 of piston 40 can also be provided with a lower-sealing rim 45 which sealingly engages interior surface 28. Extending radially outward from top-side 42 and bottom-side 44 of piston 40 are upper-sealing rim 43 and lower-sealing rim 45, respectively. Preferably, upper-sealing rim 43 and lower-sealing rim 45 prevent the product stored in variable volume portion 22 from leaking past piston 40 toward actuating end 26 of housing 20 or any other part of chamber 21. The sealing engagement and the frictional forces between upper-sealing rim 43 and lower-sealing rim 45 with interior surface 28 inhibit rotation of piston 40. Thus, piston 40 is generally limited to translational movement. These frictional forces can be increased or decreased by varying the amount of surface contact between upper-sealing rim 43 or lower-sealing rim 45 and interior surface 28.

Housing 20, as shown, is cylindrical in shape having a generally circular cross-section. Alternatively, housing 20 may have a generally oval cross-section or even an irregular cross-section. When chamber 21 within housing 20 is non-circular in cross-section, the contour or cross-sectional shape of chamber 21 further prevents rotation of piston 40, since piston 40 preferably has the same contour as chamber 21. Preferably piston 40 is constructed from a fluorinated high-density polyethylene (HDPE) although many other flexible polymers can also be used.

Figure 3:
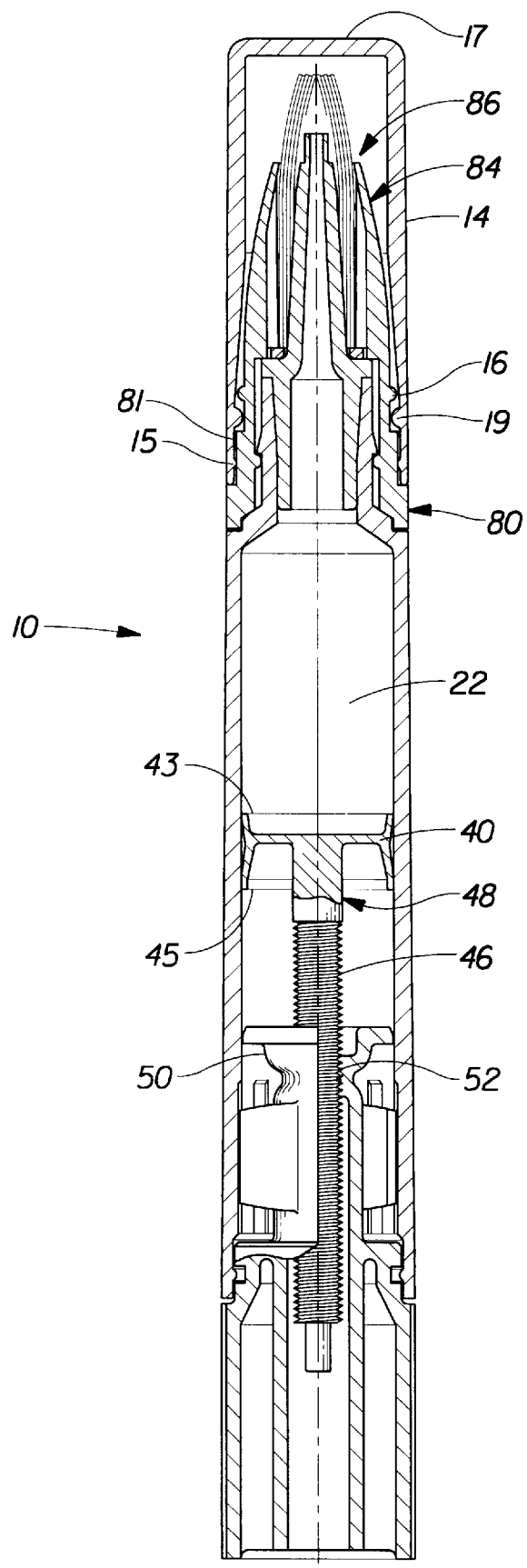
FIG. 3 is a vertical, cross-sectional view of the dispensing device seen in FIG. 1 with the cap installed and having an alternative embodiment of the product elevator.

Piston 40 also has a threaded rod 46 extending therefrom, opposite top-side 42. Thus, threaded rod 46 extends from bottom-side 44 of piston 40 toward actuating end 26 of housing 20. Preferably threaded rod 46 is made from an acetal. Upper-end 47 of threaded rod 46 is fixedly attached to bottom-side 44 of piston 40. Thus both threaded rod 46 and piston 40 move in unison and that movement is limited to axial translation. The combination of piston 40 being attached to threaded rod 46 forms a product elevator 48 which functions to move the product by pushing it out of variable volume portion 22 of chamber 21 in housing 20. As seen in FIG. 3, product elevator 48 can be a single component which includes threaded rod 46 being integrally formed with piston 40. In the preferred embodiment, seen in FIG. 2, piston 40 and threaded rod 46 can be separate components. In order to limit the axial travel of product elevator 48, a rod stop 49 can be provided on threaded rod 46 at the end opposite upper-end 47 of threaded rod 46. The amount of travel of product elevator 48 can also be limited by product elevator 48 or piston 40 simply bottoming out in the variable volume portion 22 of chamber 21. Alternative methods of limiting axial travel can be used, such as, threaded rod 46 can be partially threaded, threaded rod 46 or piston 40 can be made shorter or longer, piston 40 can be provided with a protrusion on top side 42, or various other methods known in the art for limiting axial travel of similar components.

As illustrated in FIG. 2, an actuator 50 having a threaded aperture 52 therethrough is provided on a hand wheel 51. Preferably, threaded aperture 52 is concentric within actuator 50. Actuator 50 engages interior surface 28 at actuating end 26 of housing 20 and is adapted to rotate with respect to housing 20 in only one direction, that being an advancing direction. Since the threads on threaded rod 46 mate with threaded aperture 52, threaded rod 46 engages with threaded aperture 52 such that advancement of piston 40 toward dispensing end 24 of housing 20 occurs when actuator 50 is rotated, thereby causing the product to be dispensed from dispensing device 10.

Hand wheel 51 is preferably a single integral component which includes both actuator 50 and a grip portion 54. As such, hand wheel 51 includes actuator 50 having a threaded aperture 52 therethrough and has a grip portion 54 connected to actuator 50. Grip portion 54 extends from actuating end 26 of housing 20 and preferably has a grooved or knurled surface in order for the user to easily grasp hand wheel 51. Preferably, a cavity 59 extends axially through grip portion 54 of hand wheel 51 in order to provide access to threaded aperture 52. More preferably, threaded aperture 52 is smaller than rod stop 49 while cavity 59 allows rod stop 49 to pass therethrough. Actuator 50 includes a groove 56 which engages with or is captured by lip 30 on interior surface 28 at actuating end 26 of housing 20 such that actuator 50 is rotatable but cannot move axially relative to interior surface 28. This arrangement allows rotation of hand wheel 51 while prohibiting axial movement of hand wheel 51. Preferably hand wheel 51 is unitarily formed using an injection molding process from a plastic material such as ABS which is commercially available as MAGNUM™ 9015 from DOW Chemicals or a PP homopolymer or copolymer with a calcium carbonate filler having a loading level of from about 5% to about 40% by weight can also be used.

Figure 4:
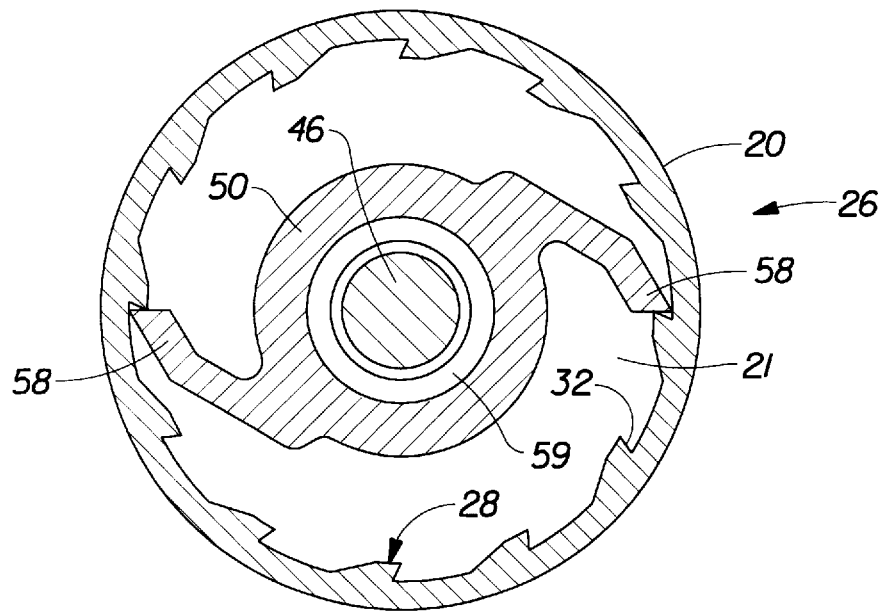
FIG. 4 is a full cross-section of the dispensing device taken along line 4—4 of FIG. 2.

Actuator 50 on hand wheel 51 also includes at least one resilient arm 58 extending radially outwardly therefrom and can be inclined radially toward interior surface 28. Resilient, as used herein, refers to the nature of resilient arm 58 which urges it to return to its original position upon being deflected from its original position. Resilient arms 58 can be better seen with reference to FIG. 4 in which a full cross-section of dispensing device 10 taken along line 4—4 of FIG. 2 is shown. Resilient arms 58 engage detents 32 located on interior surface 28 such that actuator 50 is rotatable in an advancing direction but not in an opposite direction. Preferably, actuator 50 has at least two resilient arms 58. More preferably, resilient arms 58 are oriented at an angle directed radially outwardly toward interior surface 28 such that resilient arms 58 engage detents 32 and are deflected inward by detents 32 when hand wheel 51 is rotated in an advancing direction. When hand wheel 51 is rotated in the advancing direction, the engagement of threaded rod 46 with threaded aperture 52 causes piston 40 to translate toward dispensing end 24. Any attempted rotation of hand wheel 51 in the opposite direction is limited and causes resilient arms 58 to abut detents 32 which prevents rotation of hand wheel 51 in an opposite direction. Since hand wheel 51 is limited to rotation in only the advancing direction, product elevator 48 is only allowed to translate in one direction. Thus, dispensing device 10 is unidirectional in nature.

Hand wheel 51 is rotated by the user in order to dispense the product in a controlled manner from dispensing device 10. Preferably, detents 32 are radially spaced about interior surface 28 and resilient arms 58 engage and disengage with detents 32 as hand wheel 51 is rotated in the advancing direction. Each engagement of resilient arms 58 with detents 32 provides a certain incremental translational movement of piston 40 and thus provides incremental movement of product elevator 48. The radial spacing between detents 32 can be varied to provide more or less axial translation of piston 40 with each increment of rotation. For example, detents 32 can be uniformly spaced apart, irregularly spaced, or even intermittently spaced at varying distances about interior surface 28. The amount of product dispensed from variable volume portion 22 is controlled by the incremental movement of piston 40 and an incremental volume of product is dispensed thus achieving incremental dosing of the product. This incremental dosing assists the user in dispensing an accurate or regulated amount of product and helps avoid messy or wasteful over-dispensing.

One advantage of this configuration is that an audible sound is produced as hand wheel 51 is rotated in the advancing direction. This clicking sound is created when resilient arm 58 springs back against detent 32 and contacts interior surface 28 of housing 20 during rotation of actuator 50. Additionally, a tactile signal is produced as hand wheel 51 is rotated in the advancing direction. The feel of intermittent resistance to rotation is created when tension is created by resilient arm 58 being deflected inward while riding over interior surface 28 between each detent 32. This tension is released when resilient arm 58 springs back outward toward and into detent 32. For example, an incremental dose is achieved by rotating hand wheel 51 a certain number of clicks which can be specified in order to provide accurate dosing of the product.

An applicator 80 can be attached at dispensing end 24 of housing 20 in fluid communication with variable volume portion 22 of chamber 21 such that the product is dispensed through applicator 80. Applicator 80 is hollow and includes ferrule 82 and application portion 84. Preferably applicator 80 is constructed of a plastic material such as PP, PE, polyethylene terapthalate (PET), nylon, or even a polyester like those commercially available as HYTREL™ 5526 by DuPont. Ferrule 82 is located opposite application portion 84 and is attached to dispensing end 24 of housing 20. Ferrule 82 includes an internal surface 85 having a bead 89. Bead 89 mates with ridge 36 on dispensing end 24 forming a snap-fit 79 engagement between ferrule 82 and dispensing end 24 thereby attaching applicator 80 to housing 20. Application portion 84 of applicator 80 has at least one orifice 86 therein in order to dispense the product through applicator 80. Preferably orifice 86 can have a diameter of from between about 0.25 mm (0.01 inch) to about 5 mm (0.2 inch).

Referring again to FIG. 2, a preferred embodiment is shown in which application portion 84 has an orifice 86 with fiber bristles 72 extending therethrough. Fiber bristles 72 of this type can be tapered and preferably fiber bristles 72 have a thickness or diameter of from about 0.1 mm (0.004 inch) to about 0.05 mm (0.002 inch). These fiber bristles 72 can be made from various materials but preferably are made of a plastic such as nylon, and more preferably made of polybutylene terapthalate (PBT). The amount which fiber bristles 72 extend beyond application portion 84 can be easily varied by changing the length of fiber bristles 72 or the thickness of the adjoining parts.

In this preferred embodiment, seen in FIG. 2, an interior shoulder 88 and a platform lock 95 are formed within applicator 80. Preferably platform lock 95 is spaced axially toward orifice 86 while also being spaced radially inward from interior shoulder 88 in a stair-stepped fashion. Platform lock 95 is in the form of four inwardly protruding struts being equally spaced apart. Alternatively, platform lock 95 can be in the form of any radially inward protrusion. A transition piece 90 having an edge 96 extending radially therefrom is positioned within dispensing end 24 of housing 20 such that edge 96 is captured between the interior shoulder 88 and dispensing end 24 of housing 20. Preferably edge 96 separates transition piece 90 into an upper transition 97 and a lower transition 93. Transition piece 90 can be constructed of a fluorinated HDPE or some other flexible polymer. Transition piece 90 has a passageway 92 therethrough which places orifice 86 and fiber bristles 72 in fluid communication with variable volume portion 22 of chamber 21. Within passageway 92 can be located a second reducer 25, similar to first reducer 23, which acts to reduce or decrease the cross section through which product passes when being dispensed and thereby functioning to reduce the flow area through passageway 92. Preferably, transition piece 90 is positioned such that it extends through ferrule 82 into application portion 84 of applicator 80. Alternatively, transition piece 90 having passageway 92 therethrough can extend through applicator 80 and beyond application portion 84. In this preferred embodiment, an annular platform 94 having a central opening therein is affixed to fiber bristles 72 forming a brush tip 74. Upper transition 97 of transition piece 90 extends through the central opening in annular platform 94. Annular platform 94 is captured between edge 96 on transition piece 90 and platform lock 95 such that annular platform 94 positions fiber bristles 72 of brush tip 74 relative to orifice 86 in application portion 84.

Figures 5, 6:
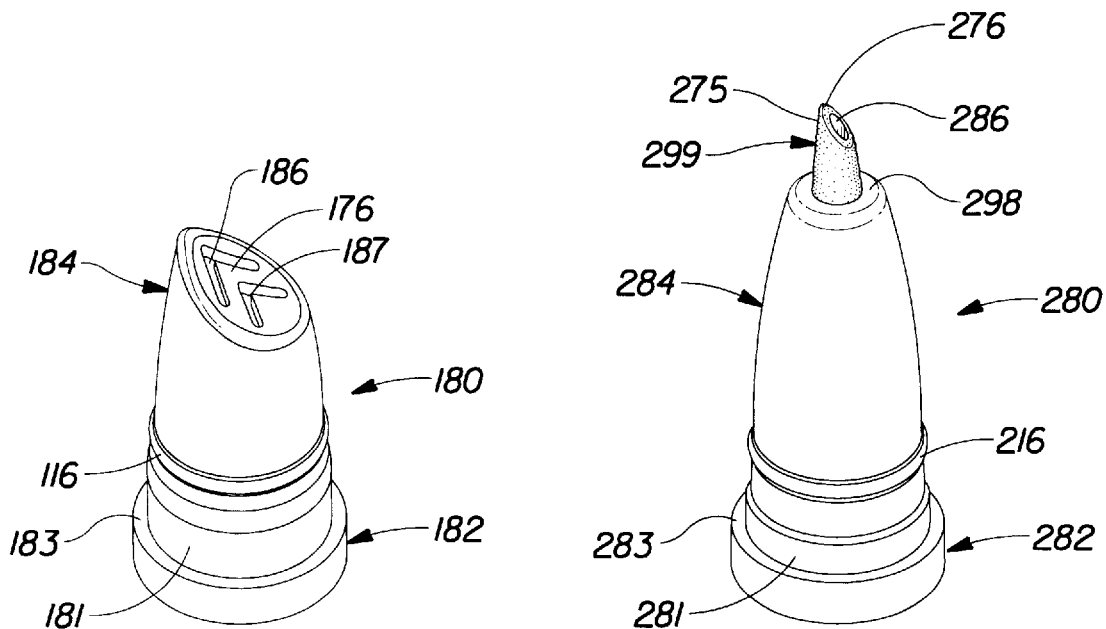
FIG. 5 is a perspective view showing a first alternative embodiment of an applicator according to the present invention.
FIG. 6 is a perspective view showing a second alternative embodiment of an applicator according to the present invention.

FIG. 5 illustrates a first alternative embodiment which includes an applicator 180, that is hollow, having a ferrule 182 and an application portion 184. Application portion 184 has an application surface 176 at the end thereof opposite ferrule 182. Application portion 184 is substantially bullet shaped and application surface 176 may be generally flat, oval, elongated, elliptical, concave, hemispherical, hyperbolic, parabolic, or rounded in shape and contour. Application surface 176 has at least one orifice 186 therethrough. Preferably, at least one orifice 186 is in the shape of a chevron 187.

Figure 7:
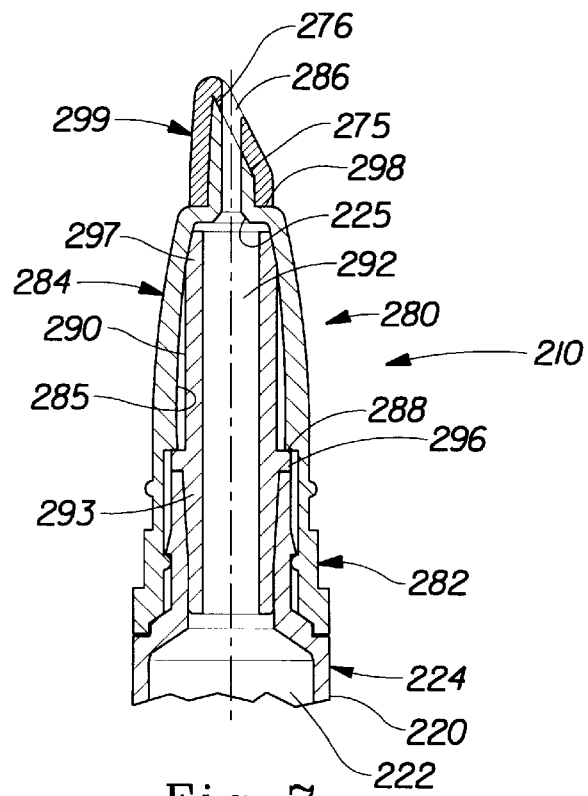
FIG. 7 is a partial vertical, cross-sectional view of the dispensing device showing the second alternative embodiment of FIG. 6.

FIG. 6 illustrates a second alternative embodiment which includes an applicator 280, that is hollow, having a ferrule 282 and an application portion 284. Application portion 284 having an external shoulder 298 at the end thereof opposite ferrule 282. External shoulder 298 extends radially inward to an axially protruding distribution head 299. Distribution head 299 is cylindrical in shape and has an application surface 276 on the end thereof. Application surface 276 can be inclined from a position perpendicular to the axis of applicator 280 and preferably the angle of incline is from about 100° to about 180°, more preferably, the angle of incline is from about 110° to about 125°. Referring now to FIG. 7, application surface 276 has an orifice 286 therein. Transition piece 290 has an edge 296 extending radially therefrom. Edge 296 separates transition piece 290 into an upper transition 297 and a lower transition 293. Transition piece 290 is positioned within dispensing end 224 of housing 220 such that edge 296 is captured between interior shoulder 288 of applicator 280 and dispensing end 224 of housing 220. Transition piece 290 is positioned such that it extends through ferrule 282 into application portion 284 of applicator 280 and upper transition 297 seals against or sealingly engages internal surface 285 of applicator 280. Transition piece 290 has a passageway 292 therethrough which places orifice 286 in fluid communication with variable volume portion 222 in order to allow product to flow from variable volume portion 222 and out through applicator 280. Within applicator 280 and adjacent to external shoulder 298 is a second reducer 225 which acts to reduce or decrease the flow area through which product passes when being dispensed.

In these first and second alternative embodiments, flocking 275 can be applied to distribution head 299, as well as application surface 276. Flocking 275 is a mat of thin short fibers substantially perpendicular to the applied surface. This achieves a velvety feel when flocking 275 is touched by a user. Preferably flocking 275 comprises nylon or polyester fibers. Each fiber of flocking 275 preferably has a diameter of about 1 to about 5 denier and a length of about 0.25 mm (0.01 inch) to about 1.5 mm (0.06 inch). The cross-sectional shape of each fiber of flocking 275 may be circular, c-shaped, x-shaped, elliptical, irregular, or the like.

Figure 8:
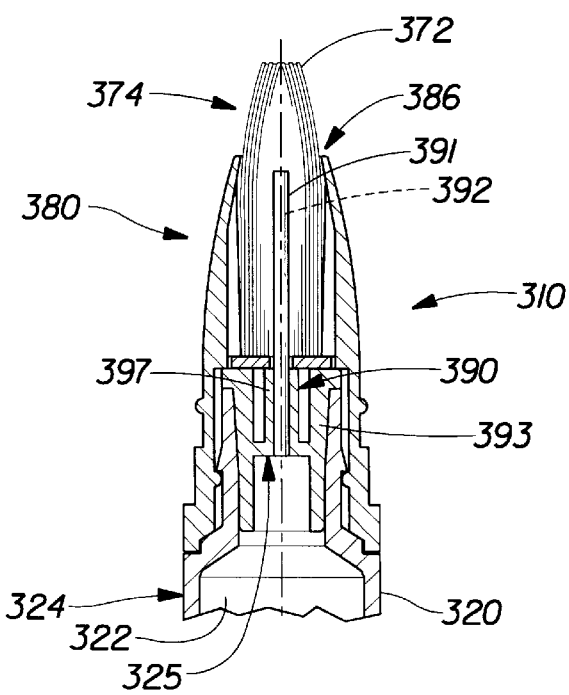
FIG. 8 is a partial vertical, cross-sectional view showing a third alternative embodiment of an applicator according to the present invention.

FIG. 8 illustrates a third alternative embodiment which includes a transition piece 390 that is made of two separate parts. In this third alternative embodiment, upper transition 97 of FIG. 2 is replaced by a tube 391 and lower transition 393 includes an open fitment 397 configured to receive tube 391. Tube 391 is hollow and includes a passageway 392 that connects fiber bristles 372 and orifice 386 to variable volume portion 322 so that they are in fluid communication with each other. Alternatively, tube 391 or upper transition 97 can have a closed end with a plurality of holes spaced along the length or circumference or tube 391 can be a tube made of porous plastic. Such an arrangement can assist in evenly distributing the product being dispensed from variable volume portion 322.

Figure 9:
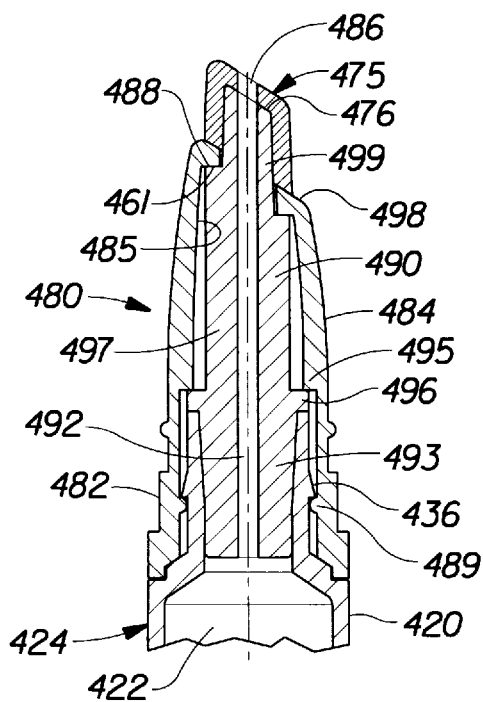
FIG. 9 is a partial vertical, cross-sectional view showing a fourth alternative embodiment of an applicator according to the present invention.

FIG. 9 illustrates a fourth alternative embodiment which includes an applicator 480, similar to that shown in FIG. 7, having a ferrule 482 and an application portion 484. In this fourth alternative embodiment, application portion 484 has an external shoulder 498 at the end thereof opposite ferrule 482. External shoulder 498 extends radially inward and defines the periphery of an opening which extends through external shoulder 498 of application portion 484. External shoulder 498, as shown, is inclined from a position perpendicular to the axis of applicator 480 and preferably external shoulder 498 has an arcuate contour being concave, convex, or the like. Transition piece 490 has an edge 496 extending radially therefrom which separates transition piece 490 into an upper transition 497 and a lower transition 493. The upper transition 497 includes a distribution head 499 integral thereto. Distribution head 499 can be substantially conical, cylindrical, frusta-conical, or the like in shape and contour. Distribution head 499 includes an application surface 476 on the end thereof and application surface 476 has an orifice 486 therein. Application surface 476 can be perpendicular to or inclined from a position perpendicular to the axis of applicator 480. Flocking 475 can be applied to distribution head 499 or application surface 476. Transition piece 490 is positioned within dispensing end 424 of housing 420 such that edge 496 is captured between interior shoulder 495 of applicator 480 and dispensing end 424 of housing 420. Transition piece 490 is positioned such that it extends through ferrule 482 into and through application portion 484 and distribution head 499 protrudes through the opening in external shoulder 498 exposing distribution head 499 and application surface 476. Ferrule 482 includes a bead 489 on internal surface 485 and dispensing end 424 includes a corresponding ridge 436. Bead 489 engages with ridge 436 in order to attach applicator 480 and transition piece 490 onto housing 420. When applicator 480 and transition piece 490 are attached to housing 420, seal face 461 on upper transition 497 sealingly abuts seal lip 488 on internal surface 485 of applicator 480 and thereby sealingly engages upper transition 497 and applicator 480. Transition piece 490 has a passageway 492 therethrough which places orifice 486 in fluid communication with variable volume portion 422 in order to allow product to flow from variable volume portion 422 and out applicator 480 through distribution head 499.

Figure 10:
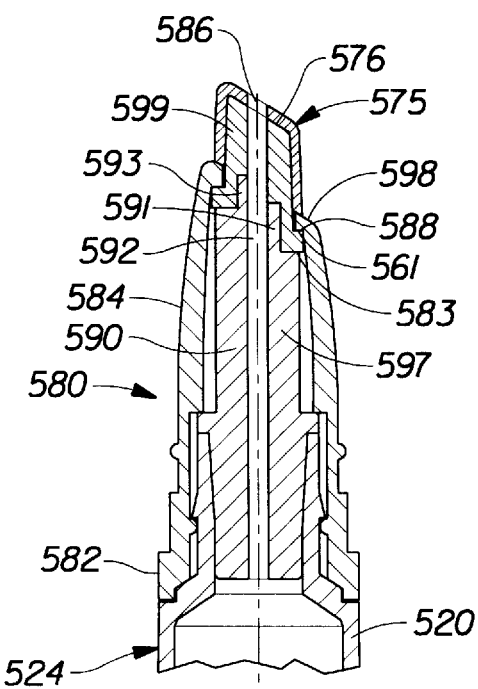
FIG. 10 is a partial vertical, cross-sectional view showing a fifth alternative embodiment of an applicator according to the present invention.

FIG. 10 illustrates a fifth alternative embodiment which includes an applicator 580, similar to that shown in FIG. 9, having a ferrule 582 and an application portion 584 with an external shoulder 598 defining an opening therethrough. In this fifth alternative embodiment, distribution head 599 is a separate component from transition piece 590 and thus distribution head 599 can be made of a different material than transition piece 590. Preferably distribution head 599 is made of a softer or more resilient material than transition piece 590. Transition piece 590 has a passageway 592 therethrough and a seal face 583 that extends radially inward to a substantially cylindrical sleeve 591 at the end of upper transition 597. Distribution head 599 includes an application surface 576 having an orifice 586 therethrough on one end thereof and a recess 593 on the other end thereof with a peripheral rim 561 extending radially outward of recess 593. Recess 593 is configured to sealingly engage with sleeve 591 of transition piece 590 and to align passageway 592 with orifice 586 when distribution head 599 is installed on transition piece 590. Transition piece 590 is positioned such that it extends through ferrule 582 and into application portion 584 allowing distribution head 599 to protrude through the opening in external shoulder 598 exposing both distribution head 599 and application surface 576. Flocking 575 can be applied to distribution head 599 or to application surface 576. A seal lip 588 is provided on the inboard side of external shoulder 598 and peripheral rim 561 is sealingly captured between seal face 583 and seal lip 588 when applicator 580 and transition piece 590 with distribution head 599 are attached to dispensing end 524 of housing 520. Various other types and shapes of applicators 580 may also be attached to dispensing end 524 of housing 520 of this dispensing device, for example, a roller ball, mesh top, porous foam, sponge, elastomeric tip having a slit, bullet shaped tip, chisel shaped tip, porous dome, capillary fibers, or similar applicator may be used.

Referring back to FIG. 3, cap 14 is shown in the installed position on applicator 80 of dispensing device 10 thereby sealingly enclosing orifice 86 and application portion 84 of applicator 80. Preferably closed-end 17 of cap 14 is spaced away from and does not contact applicator 80. Cap 14 is removable, as shown in FIG. 1. An applicator rib 16 is provided on applicator 80 and a cap locking rib 19 is provided on the interior of cap 14. Cap locking rib 19 can be in the form of an intermittent or continuous protrusion. When cap 14 is installed onto the applicator 80, applicator rib 16 and cap locking rib 19 cooperate to removably affix cap 14 onto applicator 80. In order to attach cap 14 in place on applicator 80 open-end 18 (FIG. 1) engages applicator 80 such that applicator rib 16 engages with cap locking rib 19. Accordingly, a user can simply snap cap 14 into place on applicator 80 when dispensing device 10 is not in use and can also easily remove cap 14 in order to access applicator 80. In the embodiment shown in FIG. 3, cap locking rib 19 or applicator rib 16 deflects slightly and then returns to its normal position to ensure cap 14 stays in place until the user removes cap 14 in order to dispense the product. The interior of cap 14 is also provided with a sealing bead 15 which is positioned so as to align with sealing land 81 on applicator 80. Sealing bead 15 on cap 14 engages with sealing land 81 of applicator 80 providing sealing engagement of cap 14 and applicator 80 such that when cap 14 is installed on applicator 80 an airtight seal is created between cap 14 and applicator 80. Thus, cap 14 sealingly engages ferrule 82 on applicator 80 prohibiting any product escape or drying out of the product contained within variable volume portion 22 of dispensing device 10. Preferably, a smooth or flush contour is generated between the exterior of cap 14 and applicator 80 and housing 20 when cap 14 is in the installed position.

Assembly of dispensing device 10, shown in FIG. 2 and 3, is easily accomplished and one can start by threadably connecting product elevator 48 to hand wheel 51. Threaded rod 46 is engaged with threaded aperture 52 in a manner that allows bottom-side 44 of piston 40 to be attached to upper-end 47 of threaded rod 46 if needed. Product elevator 48 and hand wheel 51 are then inserted into actuating end 26 of housing 20 such that groove 56 and lip 30 engage, thereby rotatably connecting hand wheel 51 in place while also positioning piston 40 within chamber 21 and forming variable volume portion 22. Care should be taken during assembly to orient resilient arms 58 for proper engagement with detents 32 in order to avoid loading or creep of resilient arms 58. Variable volume portion 22 can then be filled with product. Transition piece 90, if needed, can be placed in dispensing end 24 of housing 20 and, if needed, brush tip 74 can be installed over transition piece 90. Applicator 80 can be attached at dispensing end 24, over transition piece 90 and capturing brush tip 74, if installed. Cap 14 can also be removably attached on applicator 80. Alternatively, assembly may also be initiated by inverting housing 20 such that actuating end 26 is facing upward and then placing piston 40 into chamber 21 of housing 20 through actuating end 26 such that bottom-side 44 is facing upward. Hand wheel 51 can then be inserted into actuating end 26 of housing 20 and upper-end 47 of threaded rod 46 can be attached to bottom-side 44 of piston 40 through cavity 59 while engaging threaded aperture 52 of hand wheel 51.

Although various products such as fluids, flowable materials, semisolids, or liquids can be dispensed utilizing dispensing device 10 described herein, of particular interest are cosmetics. Cosmetics can be, for example, eye shadow, liquid foundation, lip color, lip stick, mascara, nail color, powder, deodorant, antiperspirant, or a variety of other color cosmetics, and the like. A uniform thin film is achieved when a cosmetic composition is dispensed and applied using this dispensing device 10. Examples of cosmetic compositions capable of utilizing dispensing device 10 include the following:

Example 1: Lip Composition

| Ingredients | Weight (%) |
|---|---|
| Group A: | |
| Silicone Gum[1] | 12.60 |
| Isododecane[2] | 12.60 |
| Group B: | |
| Isododecane[2] | 43.38 |
| Bentonite Clay[4] | 1.00 |
| Propylene Carbonate | 0.32 |
| Red #6 Calcium Lake | 1.00 |
| Red #7 Barium Lake | 3.00 |
| Titanium Dioxide | 1.50 |
| Mica | 2.20 |
| Organosiloxane resin[3] | 22.40 |

[1]2,500,000 cSt Dimethicone Gum available as SE 63 from General Electric.
[2]Permethyl 99A available from Permethyl Corp.
[3]MQ Resin (0.7:1 ratio M:Q) available as 1170-002 from General Electric.
[4]Bentone 38 available from Rheox.

Combine Group A ingredients together in a beaker and mix with a propeller mixer until uniform. Combine all Group B ingredients except the propylene carbonate and hand-mix to roughly incorporate the dry powders. Homogenize the entire formulation using a Ross ME 100 LC homogenizer at about 7500 rpm until all pigments are fully dispersed. Next, while continuing the homogenization process, slowly add the propylene carbonate until mixture thickens. Combine Group A mixture with Group B mixture in a beaker and mix with a propeller mixer until uniform. Transfer the resulting fluid to individual packages.

Example 2: Liquid Foundation

| Ingredient | Weight (%) |
|---|---|
| Group A: | |
| Organosiloxane Resin[1] | 4.48 |
| Cyclomethicone[2] | 11.11 |
| Silicone-polyether Emulsifier[3] | 10.00 |
| Group B: | |
| Silicone-Treated Titanium Dioxide | 6.50 |
| Silicone-Treated Yellow Iron Oxide | 0.28 |
| Silicone-Treated Red Iron Oxide | 0.15 |
| Silicone-Treated Black Iron Oxide | 0.06 |
| Group C: | |
| 2,500,000 cSt Silicone Gum[4] | 2.52 |
| Cyclomethicone[2] | 4.90 |
| Group D: | |
| Water | 49.50 |
| Glycerin | 10.00 |
| Methyl Paraben | 0.20 |
| 2-Phenoxyethanol | 0.30 |

[1]MQ Resin available as 1170-002 from General Electric.
[2]Cyclomethicone available as 245 fluid from Dow Corning.
[3]Silicone-Polyether Emulsifier available as DC3225C from Dow Corning.
[4]Dimethicone Gum (2,500,000 cSt) available as SE63 from General Electric.

Combine Group A and Group B ingredients together and homogenize at 9500 rpm for 15 minutes. Add Group C ingredients and homogenize at 2000 rpm for 2 minutes. Combine Group D ingredients in a separate container and mix with a propeller mixer until a clear solution forms. Add the Group D solution to the mixture of Groups A, B, and C very slowly while homogenizing at 2000 rpm. When all of the Group D solution has been incorporated, homogenize the entire mixture at 2000 rpm for an additional 10 minutes. Finally, homogenize the entire mixture at 5000 rpm for 5 minutes. Transfer the resulting fluid to individual packages.

Example 3: Mascara

| Ingredient | Weight (%) |
|---|---|
| Group A: | |
| Organosiloxane Resin[1] | 9.60 |
| Cyclomethicone[2] | 8.82 |
| Silicone-polyether Emulsifier[3] | 10.00 |
| Group B: | |
| Silicone-Treated Black Iron Oxide | 5.00 |
| Group C: | |
| 2,500,000 cSt Silicone Gum[4] | 5.40 |
| Cyclomethicone[2] | 16.18 |
| Group D: | |
| Water | 43.50 |
| Sodium Chloride | 1.00 |
| Methyl Paraben | 0.20 |
| 2-Phenoxyethanol | 0.30 |

[1]MQ Resin available as 1170-002 from General Electric.
[2]Cyclomethicone available as 244 fluid from Dow Corning.
[3]Silicone-Polyether Emulsifier available as DC3225C from Dow Corning.
[4]Dimethicone Gum (2,500,000 cSt) available as SE63 from General Electric.

Combine Group A and Group B ingredients together and homogenize at 9500 rpm for 15 minutes. Add Group C ingredients and homogenize at 2000 rpm for 2 minutes. Combine Group D ingredients in a separate container and mix with a propeller mixer until a clear solution forms. Add the Group D solution to the mixture of Groups A, B, and C very slowly while homogenizing at 2000 rpm. When all of the Group D solution has been incorporated, homogenize the entire mixture at 2000 rpm for an additional 10 minutes. Finally, homogenize the entire mixture at 5000 rpm for 5 minutes. Transfer the resulting fluid to individual packages.

Example 4: Shear Lip Tint Composition

| Ingredients | Weight (%) |
|---|---|
| Group A: | |
| Silicone Gum[1] | 11.88 |
| Isododecane[2] | 54.45 |
| Group B: | |
| Organosiloxane resin[3] | 20.78 |
| Red #6 Calcium Lake | 0.50 |
| Red #7 Barium Lake | 0.50 |
| Gemtone Sunstone[5] | 0.50 |
| Timiron MP-115 Pearl[6] | 0.50 |
| Bentone Gel[4] | 10.89 |

[1]2,500,000 cSt Dimethicone Gum available as SE 63 from General Electric.
[2]Permethyl 99A available from Permethyl Corp.
[3]MQ Resin (0.7:1 ratio M:Q) available as 1170-002 from General Electric.
[4]VS-5 PC available from Rheox.
[5]Gemtone Sunstone available from Mearl Corporation.
[6]Timiron MP-115 Pearl available from Mearl Corporation.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

Example 5: Liquid Eye Liner Composition

| Ingredient | Weight (%) |
|---|---|
| Group A: | |
| Organosiloxane Resin[1] | 8.90 |
| Isododecane[2] | 14.90 |
| Group B: | |
| Black Iron Oxide | 20.00 |
| Propylparaben | 0.10 |
| Group C: | |
| 100,000 cSt Silicone Fluid[3] | 11.10 |
| Isododecane[2] | 33.00 |
| Group D: | |
| Isododecane[2] | 10.00 |
| Trihydroxystearin | 2.00 |

[1]MQ Resin (0.7:1 ratio M:Q) available as 1170-002 from General Electric.
[2]Permethyl 99A available from Permethyl Corp.
[3]Dimethicone Fluid (100,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57°–60° C. for about 3 minutes. Remove from the heat and homogenize for approximately 5 minutes or until a gel develops. Finally, add the Group D mixture to the rest of the batch and heat the entire mixture to 57°–60° C. for about 7–10 minutes while mixing with a propeller mixer. Remove the batch from the heat and allow it to cool to room temperature while mixing with a propeller mixer. Transfer the resulting fluid to individual packages.

Example 6: Eye Shadow Composition

| Ingredient | Weight (%) |
|---|---|
| Group A: | |
| Organosiloxane Resin[1] | 22.14 |
| Isododecane[2] | 14.90 |
| Group B: | |
| Flamenco Gold Pearl | 0.60 |
| Flamenco Superpearl | 0.84 |
| Titanium Dioxide | 0.94 |
| Gemtone Copper | 0.41 |
| Gemtone Sunstone | 1.21 |
| Propylparaben | 0.10 |
| Group C: | |
| 1,000 cSt Silicone Fluid[3] | 13.86 |
| Isododecane[2] | 33.00 |
| Group D: | |
| Isododecane[2] | 10.00 |
| Trihydroxystearin | 2.00 |

[1]MQ Resin (0.7:1 ratio M:Q) available as 1170-002 from General Electric.
[2]Permethyl 99A available from Permethyl Corp.
[3]Dimethicone Fluid (1,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57°–60° C. for about 3 minutes. Remove from the heat and homogenize for approximately 5 minutes or until a gel develops. Finally, add the Group D mixture to the rest of the batch and heat the entire mixture to 57°–60° C. for about 7–10 , minutes while mixing with a propeller mixer. Remove the batch from the heat and allow it to cool to room temperature while mixing with a propeller mixer. Transfer the resulting fluid to individual packages.

Although particular versions and embodiments of the present invention have been shown and described, various modifications can be made to this twist-up dispensing device 10 without departing from the teachings of the present invention. For example, the various connections between the components can be fabricated using methods other than snapping the components together, including, threaded engagement, adhesive bonding, welding, and the like. The terms used in describing the invention are used in their descriptive sense and not as terms of limitation, it being intended that all equivalents thereof, be included within the scope of the appended claims.

What is claimed is:

1. A twist-up dispensing device for dispensing a product, said dispensing device comprising:
a) a hollow housing defining a chamber having an open dispensing end and an actuating end, said actuating end having an interior surface, said interior surface is cylindrical and includes a lip and at least one detent; and
b) a piston located within said chamber, said piston being limited to translational movement within said chamber, said piston having a top side facing said dispensing end of said housing and having a threaded rod extending therefrom opposite said top side, a variable volume portion of said chamber formed between said chamber and said top side of said piston, said variable volume portion for storing said product; and c) a hand wheel including a grip portion and an actuator, said hand wheel being a single integral component unitarily formed from a plastic material, said actuator having a threaded aperture therethrough, said threaded aperture being concentric in said actuator, said actuator engaging said interior surface at said actuating end of said housing and being adapted to rotate with respect to said housing in only one direction, said actuator includes a groove engaged with said lip such that said actuator is rotatable but cannot move axially relative to said interior surface, said actuator also having at least one resilient arm extending outwardly and engaging said detent such that said actuator is rotatable in an advancing direction but not in an opposite direction, said threaded rod engaging said threaded aperture such that advancement of said piston toward said dispensing end occurs when said actuator is rotated, thereby causing said product to be dispensed and achieving incremental dosing of said product.

2. The twist-up dispensing device for dispensing a product according to claim 1, wherein said interior surface includes a plurality of detents.

3. The twist-up dispensing device for dispensing a product according to claim 1, wherein said resilient arm is inclined radially toward said interior surface.

4. The twist-up dispensing device for dispensing a product according to claim 1, wherein said actuator has at least two resilient arms.

5. The twist-up dispensing device for dispensing a product according to claim 1, further comprising an applicator attached to said dispensing end of said housing in fluid communication with said variable volume portion of said chamber wherein said product is dispensed through said applicator.

6. The twist-up dispensing device for dispensing a product according to claim 5, wherein said applicator includes a ferrule and an application portion, said ferrule engaging said dispensing end of said housing and said application portion having an orifice with fiber bristles extending therethrough.

7. The twist-up dispensing device for dispensing a product according to claim 6, further comprising an annular platform affixed to said fiber bristles, an interior shoulder within said applicator, and a transition piece positioned within said dispensing end of said housing, said transition piece extending through said ferrule into said application portion of said applicator, said annular platform captured between said transition piece and said interior shoulder positioning said fiber bristles relative to said orifice in said application portion, said transition piece having a passageway therethrough placing said orifice and said fiber bristles in fluid communication with said variable volume portion of said chamber.

8. The twist-up dispensing device for dispensing a product according to claim 5, wherein said applicator comprises a ferrule and an application portion, said ferrule being attached to said dispensing end of said housing and said application portion having at least one orifice therein.

9. The twist-up dispensing device for dispensing a product according to claim 8, further comprising a cap being removable and sealingly enclosing said orifice and said application portion of said applicator.

10. The twist-up dispensing device for dispensing a product according to claim 8, wherein said dispensing end of said hollow housing includes a cylindrical exterior surface having a ridge, said ferrule includes an internal surface having a bead, said bead mating with said ridge forming a snap-fit engagement between said ferrule and said dispensing end thereby attaching said applicator to said housing.

11. The twist-up dispensing device for dispensing a product according to claim 8, wherein said application portion further comprises a fiber brush.

12. The twist-up dispensing device for dispensing a product according to claim 8, wherein said application portion further comprises a flocked application surface.

13. The twist-up dispensing device for dispensing a product according to claim 12, wherein at least one orifice is in the shape of a chevron.

14. The twist-up dispensing device for dispensing a product according to claim 1, wherein said product comprises a fluid.

15. The twist-up dispensing device for dispensing a product according to claim 14, wherein said fluid comprises a cosmetic.

16. The twist-up dispensing device for dispensing a product according to claim 1, wherein said threaded rod is integrally formed with said piston.

17. The twist-up dispensing device for dispensing a product, said dispensing device comprising:

a) a hollow housing defining a chamber having an open dispensing end and an actuating end, said actuating end having an interior surface, said interior surface is cylindrical and includes a lip and a plurality of detents; and b) a piston located within said chamber, said piston being limited to translational movement within said chamber, said piston having a top side facing said dispensing end of said housing and having a threaded rod extending therefrom opposite said top side, a variable volume portion of said chamber formed between said chamber and said top side of said piston, said variable volume portion for storing said product; and c) a hand wheel including a grip portion and an actuator, said hand wheel being a single integral component unitarily formed from a plastic material, said actuator having a threaded aperture therethrough, said threaded aperture being concentric in said actuator, said actuator engaging said interior surface at said actuating end of said housing and being adapted to rotate with respect to said housing in only one direction, said actuator includes a groove engaged with said lip such that said actuator is rotatable but cannot move axially relative to said interior surface, said actuator also having at least one resilient arm extending outwardly and engaging a said detent such that said actuator is rotatable in an advancing direction but not in an opposite direction, said threaded rod engaging said threaded aperture such that advancement of said piston toward said dispensing end occurs when said actuator is rotated, thereby causing said product to be dispensed in an incremental manner; and d) an applicator attached to said dispensing end of said housing in fluid communication with said variable volume portion of said chamber wherein said product is dispensed through said applicator.

* * * * *